United States Patent
Yin

(10) Patent No.: US 9,481,867 B2
(45) Date of Patent: Nov. 1, 2016

(54) METHOD OF RAPIDLY INDUCING LARGE-SCALE AND HIGH-PURITY MESENCHYMAL STEM CELLS TO TRANSDETERMINE INTO HEMATOPOIETIC STEM CELLS

(71) Applicant: BEIJING GINKGO BIOSCIENCE CO., LTD., Beijing (CN)

(72) Inventor: Qinwei Yin, Beijing (CN)

(73) Assignee: BEIJING GINKO BIOSCIENCE CO., LTD., Beijing (CN)

( * ) Notice: Subject to any disclaimer, the term of this patent is extended or adjusted under 35 U.S.C. 154(b) by 0 days.

(21) Appl. No.: 14/343,390

(22) PCT Filed: Mar. 4, 2013

(86) PCT No.: PCT/CN2013/072150
§ 371 (c)(1),
(2) Date: Mar. 7, 2014

(87) PCT Pub. No.: WO2014/114023
PCT Pub. Date: Jul. 31, 2014

(65) Prior Publication Data
US 2015/0315545 A1   Nov. 5, 2015

(30) Foreign Application Priority Data

Jan. 25, 2013 (CN) .......................... 2013 1 0028871

(51) Int. Cl.
| | | |
|---|---|---|
| C12N 5/00 | (2006.01) | |
| C12N 15/63 | (2006.01) | |
| C12N 5/0789 | (2010.01) | |
| C12N 15/11 | (2006.01) | |

(52) U.S. Cl.
CPC ........... *C12N 5/0647* (2013.01); *C12N 15/111* (2013.01); *C12N 2310/141* (2013.01); *C12N 2320/30* (2013.01); *C12N 2501/105* (2013.01); *C12N 2501/11* (2013.01); *C12N 2501/115* (2013.01); *C12N 2501/125* (2013.01); *C12N 2501/135* (2013.01); *C12N 2501/145* (2013.01); *C12N 2501/15* (2013.01); *C12N 2501/17* (2013.01); *C12N 2501/235* (2013.01); *C12N 2501/26* (2013.01); *C12N 2501/40* (2013.01); *C12N 2501/41* (2013.01); *C12N 2501/42* (2013.01); *C12N 2501/65* (2013.01); *C12N 2506/1384* (2013.01)

(58) Field of Classification Search
CPC .............. C12N 5/0647; C12N 15/111; C12N 2501/40
USPC ........................................ 435/377, 384, 455
See application file for complete search history.

(56) References Cited

U.S. PATENT DOCUMENTS

| | | | | |
|---|---|---|---|---|
| 7,981,446 B2 * | 7/2011 | Lee | ................. | A61K 47/48246 424/491 |
| 2013/0309209 A1 * | 11/2013 | Izpisua-Belmonte | ............ | C12N 5/0647 424/93.7 |

FOREIGN PATENT DOCUMENTS

| | | | |
|---|---|---|---|
| CN | 101368180 A | * | 2/2009 |
| CN | 102131929 | * | 7/2011 |

* cited by examiner

*Primary Examiner* — Quang Nguyen

(57) ABSTRACT

A method of rapidly inducing large-scale and high-purity mesenchymal stem cells to transdetermine into hematopoietic stem cells is provided with the steps of preparing homogeneous medium of mesenchymal stem cells; combining a plurality of small RNA molecules; assembling and transfecting nanoparticles of nucleic acids and polypeptides; inducing and amplifying medium of post-transdetermined hematopoietic stem cells; and activating a plurality of hemopoiesis-related genes.

1 Claim, 7 Drawing Sheets

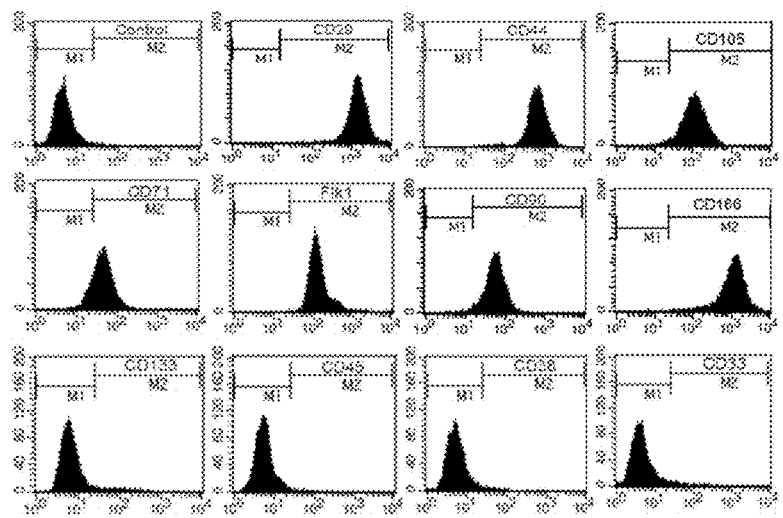
Fig.1
miR-138-1
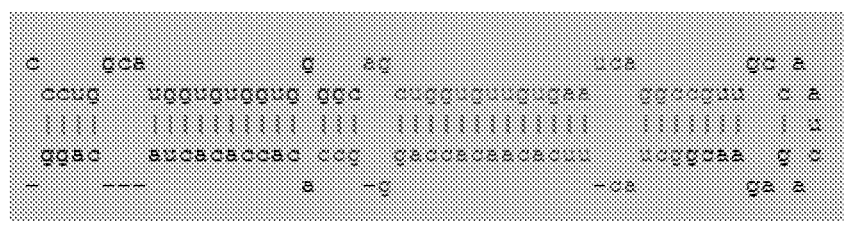
miR-138-2
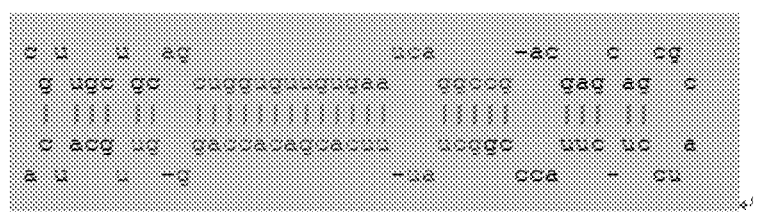
miR-433
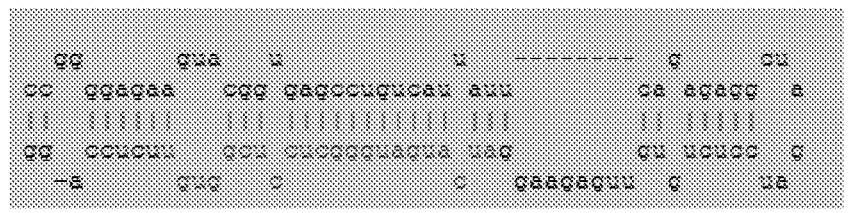
Fig. 2

| Scheme | | sRNA (µg) | Conversion Efficiency (%) | |
|---|---|---|---|---|
| | | | First | Second |
| 1 | shR-EID1 (Fig. 10) | 1 | 3±2.1 | 6±2.3 |
| | | 4 | 6±2.4 | 11±1.9 |
| 2 | siR-EID1 (Fig. 10) | 1 | 9±1.8 | 10±2.7 |
| | | 4 | 6±2.5 | 9±3.3 |
| 3 | MiRNA-138-1+miR433+miRNA138-2 | 1 | 37±4.8 | 23±4.5 |
| | | 2 | 48±6.3 | 33±4.6 |
| 4 | MiR-138-1+siEID1 | 1 | 32±5.9 | 13±3.6 |
| | | 2 | 38±4.1 | 27±1.0 |

Fig. 9

| No. | Sequence (positive-sense strand) |
|---|---|
| 1 | GGAGGACGACTACGACTATTT |
| 2 | GCATCTGTCTTGCTGGAAGCT |
| 3 | GGTTGAGCGGTTTGCACAATG |
| 4 | GGTTTGCACAATGTCGGAAAT |
| 5 | GGCGAGGAATTTGATGACTGG |
| 6 | GCGAGGAATTTGATGACTGGG |
| 7 | GCTCTTGAAGAAGCCGACAAG |
| 8 | GACAAGATGTTTCTGAGAACA |
| 9 | GGCGGGTTTCAGATGCATTAT |
| 10 | GCGGGTTTCAGATGCATTATG |
| 11 | GGTTTCAGATGCATTATGATT |
| 12 | GGACCCAACTTTCCGCTATCT |
| 13 | GCCACAGTTATCAAAGGCTAC |
| 14 | GACACTAAATGTGTGTGAATG |
| 15 | GCCCAGAAATTACCTTGGTAT |
| 16 | GCTTGTTATTTGTCATGCACC |
| 17 | GCTTCAGCTATCTAATTCACA |
| 18 | GCCCTATCAATGAGTATGTTG |
| 19 | GCCGTGGTTACCTTACTAAGA |
| 20 | GCTGAAGTTCTAGGAGAGTAA |
| 21 | GCTCCATTATAGCAGTAAAGA |
| 22 | GAACGAATATCCAATGCAACA |
| 23 | CAAATACTCACCATTGTGTTA |

Fig. 10

| Ingredient | Content |
|---|---|
| DMEM/F12 basic medium | 80-100%（v/v） |
| Sonic hedgehog (shh) | 0-1μg/ml |
| Delta1 | 0-1μg/ml |
| FGF2 | 0-1μg/ml |
| IGFBP | 0-1μg/ml |
| SCF | 0-1μg/ml |
| Angiopoietin | 0-1μg/ml |
| TPO | 0-1μg/ml |
| MBP | 0-1μg/ml |
| LIF | 0-1μg/ml |
| TGF-β | 0-1μg/ml |
| MTEPA | 0-100 μM |
| NAC | 1-5 mM |

Fig. 11

```
                              SEQUENCE LISTING

<160> NUMBER OF SEQ ID NOS: 29

<210> SEQ ID NO 1
<211> LENGTH: 99
<212> TYPE: RNA
<213> ORGANISM: Artificial Sequence
<220> FEATURE:
<223> OTHER INFORMATION: primer

<400> SEQUENCE: 1
cccuggcaug gugugguggg gcagcuggug uugugaauca ggccguugcc aaucagagaa      60
cggcuacuuc acaacaccag ggccacacca cacuacagg                            99

<210> SEQ ID NO 2
<211> LENGTH: 84
<212> TYPE: RNA
<213> ORGANISM: Artificial Sequence
<220> FEATURE:
<223> OTHER INFORMATION: primer

<400> SEQUENCE: 2
cguugcugca gcugguguug ugaaucaggc cgacgagcag cgcauccucu uacccggcua      60
uuucacgaca ccaggguugc auca                                            84

<210> SEQ ID NO 3
<211> LENGTH: 93
<212> TYPE: RNA
<213> ORGANISM: Artificial Sequence
<220> FEATURE:
<223> OTHER INFORMATION: primer

<400> SEQUENCE: 3
ccggggagaa guacggugag ccugucauua uucagagagg cuagauccuc uguuugaga      60 aggaucauga ugggcuccuc gguguucucc agg                                  93

<210> SEQ ID NO 4
<211> LENGTH: 99
<212> TYPE: RNA
<213> ORGANISM: Artificial Sequence
<220> FEATURE:
<223> OTHER INFORMATION: primer

<400> SEQUENCE: 4
cgcagaguca gcaccugugg uguggugggc cugguguugu gaaggccguu cauggacauc      60
acaccacccg gaccacaaca cuuucggcaa gcagcagaa                            99
```

-continued

```
<210> SEQ ID NO 5
<211> LENGTH: 84
<212> TYPE: RNA
<213> ORGANISM: Artificial Sequence
<220> FEATURE:
<223> OTHER INFORMATION: primer

<400> SEQUENCE: 5
cuuagucaac ccggugcgcc ugguguugug aaggccggag agccacgugg accacagcac      60
uuugggcuuc ucaauuguac cacu                                            84

<210> SEQ ID NO 6
<211> LENGTH: 93
<212> TYPE: RNA
<213> ORGANISM: Artificial Sequence
<220> FEATURE:
<223> OTHER INFORMATION: primer

<400> SEQUENCE: 6
ggguauugcu ccggagaacg ggagccuguc auauucaaga ggaggccucu ugcucucggg      60
uaguauaggu ucuccgagug ccgaagaguu gua                                  93

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
ggaggacgac tacgactatt t                                               21

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
gcatctgtct tgctggaagc t                                               21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
ggttgagcgg tttgcacaat g                                               21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
ggtttgcaca atgtcggaaa t                                               21

<210> SEQ ID NO 11
<211> LENGTH: 21
```

-continued

```
<212> TYPE: DNA
<213> ORGANISM: Artificial Sequence
<220> FEATURE:
<223> OTHER INFORMATION: primer

<400> SEQUENCE: 11
ggcgaggaat tgatgactg g                                                    21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gcgaggaatt tgatgactgg g                                                   21

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
gctcttgaag aagccgacaa g                                                   21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
gacaagatgt ttctgagaac a                                                   21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ggcgggtttc agatgcatta t                                                   21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
gcgggtttca gatgcattat g                                                   21

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
```

-continued ggtttcagat gcattatgat t                                              21

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ggacccaact ttccgctatc t                                              21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gccacagtta tcaaaggcta c                                              21

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
gacactaaat gtgtgtgaat g                                              21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gcccagaaat taccttggta t                                              21

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gcttgttatt tgtcatgcac c                                              21

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
gcttcagcta tctaattcac a                                              21

<210> SEQ ID NO 24
<211> LENGTH: 21
<212> TYPE: DNA
<213> ORGANISM: Artificial Sequence

```
<220> FEATURE:
<223> OTHER INFORMATION: primer

<400> SEQUENCE: 24
gccctatcaa tgagtatgtt g                                     21

<210> SEQ ID NO 25
<211> LENGTH: 21
<212> TYPE: DNA
<213> ORGANISM: Artificial Sequence
<220> FEATURE:
<223> OTHER INFORMATION: primer

<400> SEQUENCE: 25
gccgtggtta ccttactaag a                                     21

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
gctgaagttc taggagagta a                                     21

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
gctccattat agcagtaaag a                                     21

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
gaacgaatat ccaatgcaac a                                     21

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
caaatactca ccattgtgtt a                                     21
```

METHOD OF RAPIDLY INDUCING LARGE-SCALE AND HIGH-PURITY MESENCHYMAL STEM CELLS TO TRANSDETERMINE INTO HEMATOPOIETIC STEM CELLS

BACKGROUND OF THE INVENTION

1. Field of the Invention

The invention relates to biotechnology and more particularly to a method of rapidly inducing large-scale and high-purity mesenchymal stem cells to transdetermine into hematopoietic stem cells.

2. Description of Related Art

White adipose tissue (WAT), the main source of adipose-derived stem cell (AD-MSCs), is widely distributed in the body and abundant. Cell cloning experiment has proved that bone marrow derived mesenchymal stem cells (Bone-marrow mesenchymal stem cell, BMSCs) only is $0.2 \times 10^{-5}$-$0.1 \times 10^{-5}$ of adult bone marrow, and the cloning efficiency of stem cell obtained from adipose tissue is 100-500 times of that of BMSCs. The proportion and proliferation ability of BMSCs in bone-marrow descends with the increasing of age and incidence rate of osteoporosis, but the quantity of ADSCs in adipose tissue does not decrease with the increasing of age of the donors. The ability of amplification in vitro and renewability of ADSC is strong, and cell fusion is more than 90% after 5-7 days of primary culture, and Logarithmic growth phase occurs three times in one month, and can be passaged stably more than 20 generations; It is not special selectivity for serum when cultured in vitro, and can grow well without additives, and growth and phenotype of ADSCs is not changed after freezing of liquid nitrogen and long-term passage generations.

ADSCs has multipotent differentiation capacity, and ADSCs can directionally differentiates into a variety of tissue cells, such as osteoblast, chondrocytes, adipocytes, endothelial cells, skeletal muscle cells, cardiac cells, pancreatic endocrine-like cells, liver cells and optic nerve cells etc. under different induced culture conditions. But it is not clear whether they can be transformed into hematopoietic stem cell (HSCs) till now.

Hematopoietic stem cell is the most effective method of treating hemopathy, especially for leukemia. Leukemia has the trend of increasing significantly in China recently as same as other tumor diseases, and presents the character of younger-age trend. Leukimia accounts for 5% of malignant cancer, and incidence is in the majority in children and young people. The most effective method of treating leukemia is hematopoietic stem cell treatment. Families of patients and related sectors of society use all available resources to find a suitable matching hematopoietic stem cells, but the possibility of matching is extremely small. Therefore it is pushed the establishment of a national stem cell bank, but the expense of each bank is about 2 hundred million yuan, and its high economic cost can be imagined. But technically it is not completely rule out the possibility of immune rejection and tumorigenesis. Furthermore, the high-quality medical treatment can not be assured due to limited quantity of stem cells and lacking of non-differentiated amplification technique. For all those above-mentioned reasons, it exists urgent need for people to discover new sources of hematopoietic stem cells and to develop new techniques and methods of non-differentiated amplification of hematopoietic stem cells.

Recent research has discovered that the expression of small RNA in different types of hematopoietic cells is significantly different, and the difference plays very important regulation effect in the process of cell development. For instance, iR-181 is related with B-lymphocyte development, miR-142 and miR-223 are related with development of T-lymphocytes, miR-221 and miR-222 are related with human erythrocytopoiesis, miR-223 is related with granulocyte cell differentiation of mice, and miR-10, miR-126 and miR-17 are related with decreasing of megakaryocyte. Beyond that, people also discovered that some miRNA, such as miR-130a and miR-10a, induce cell differentiation through affecting transcription factor genes of HOXA1 gene and MAFB gene.

SUMMARY OF THE INVENTION

It is therefore one object of the invention to provide a method which capable of rapidly inducing large-scale and high-purity mesenchymal stem cells to transdetermine into hematopoietic stem cells, resolving the technical bottleneck problem of cell matching difficulties, immune rejection and quantity limitation of hematopoietic stem cells in prior art of hematopoietic stem cell of treatment.

The technical resolution of the invention is achieved in that: a method which capable of rapidly inducing large-scale and high-purity mesenchymal stem cells to transdetermine into hematopoietic stem cells comprising the steps of preparing homogeneous medium of mesenchymal stem cells; combining a plurality of small RNA molecules; assembling and transfection of nanoparticles of nucleic acids and polypeptides; inducing and amplifying medium of post-transdetermined hematopoietic stem cells; and activating multiple hemopoiesis-related genes.

As preferred technical solution, the medium refers to the medium of adding five factors of EGF, FGF-2, PDGF-BB, IGF and TGF-β into non-serum high-glucose DMEM/F12 medium.

As preferred technical solution, the medium is the medium of adding ten factors of shh, SCF, TPO, Flt3L, Delta1, IGFBP, Angiopoietin, MBP4, LIF, and TGF-β into non-serum high-glucose DMEM/F12 medium.

As preferred technical solution, the various small RNA molecules refer to miR-138-1 having the sequence of SEQ ID NO:1, miR-138-2 having the sequence of SEQ ID NO:3, miR-433 having the sequence of SEQ ID NO:5 and siR-EID1 molecule sequence targeting different loci of EID1 mRNA.

The siR-EID1 molecule sequence targeting different loci of EID1 mRNA shown in FIG. 10 comprises SEQ ID NO:7 (GGAGGACGACTACGACTATTT), SEQ ID NO:8 (GCATCTGTCTTGCTGGAAGCT), SEQ ID NO:9 (GGTTGAGCGGTTTGCACAATG), SEQ ID NO:10 (GGTTTGCACAATGTCGGAAAT), SEQ ID NO:11 (GGCGAGGAATTTGATGACTGG), SEQ ID NO:12 (GCGAGGAATTTGATGACTGGG), SEQ ID NO:13 (GCTCTTGAAGAAGCCGACAAG), SEQ ID NO:14 (GACAAGATGTTTCTGAGAACA), SEQ ID NO:15 (GGCGGGTTTCAGATGCATTAT), SEQ ID NO:16 (GCGGGTTTCAGATGCATTATG), SEQ ID NO:17 (GGTTTCAGATGCATTATGATT), SEQ ID NO:18 (GGACCCAACTTTCCGCTATCT), SEQ ID NO:19 (GCCACAGTTATCAAAGGCTAC), SEQ ID NO:20 (GACACTAAATGTGTGTGAATG), SEQ ID NO:21 (GCCCAGAAATTACCTTGGTAT), SEQ ID NO:22 (GCTTGTTATTTGTCATGCACC), SEQ ID NO:23 (GCTTCAGCTATCTAATTCACA), SEQ ID NO:24 (GCCCTATCAATGAGTATGTTG), SEQ ID NO:25 (GCCGTGGTTACCTTACTAAGA), SEQ ID NO:26

(GCTGAAGTTCTAGGAGAGTAA), SEQ ID NO:27 (GCTCCATTATAGCAGTAAAGA), SEQ ID NO:28 (GAACGAATATCCAATGCAACA), and SEQ ID NO:29 (CAAATACTCACCATTGTGTTA). As preferred technical solution, the culture of the post-transdetermined hematopoietic stem cells refers to cultivate at least 3 days as cell density of 5×10⁵/ml in the medium of inducing and amplifying hematopoietic stem cells.

Assembling of nucleic acid and polypeptide nanoparticles refers to preparation process of various small RNA molecules with polypeptide transfection reagents according to the proportion, procedure and time in example 3, and achieves the optimal inductive efficiency through transfection of once a day, totally 2 times.

As preferred technical solution, the activating multiple hemopoiesis-related genes refers to, but not limited to, Runx1, Bmi1, HoxB4, Gata1, Gata2, Gfi1, Sa114, Pu.1, Scl, Mcl, C-myc, C-myb, Kc14, Cxcr4, and Crb.

The formula of mesenchymal stem cell medium can be made to different cultivation kit, which includes cell proliferation factors and cell differentiation inhibitors needed in proliferation of different mesenchymal stem cells.

The formula of hematopoietic stem cells inducing and amplification medium can be made to different cultivation kit, which includes cell proliferation factors and cell differentiation inhibitors needed in proliferation of hematopoietic stem cells. The detailed formula is shown in FIG. 11.

The induced hematopoietic stem cells obtained by the method of the invention can be used in the treatment of blood diseases, such as aplastic anemia and leukemia.

The above and other objects, features and advantages of the invention will become apparent from the following detailed description taken with the accompanying drawings.

BRIEF DESCRIPTION OF THE DRAWINGS

FIG. 1 is specific antigens on the surface of human adipose mesenchymal stem cell. The flow cytometry analysis shows that human adipose mesenchymal stem cells are CD29, CD44, Flk1, CD90, CD105, CD71 and CD166 positive, and CD133, CD38, CD33 and CD45 negative according to the invention;

FIG. 2 is the second structure of miR-138-1 having the sequence of SEQ ID NO:1, miR-138-2 having the sequence of SEQ ID NO:3 and miR-433 having the sequence of SEQ ID NO:5 molecules according to the invention;

FIG. 9 is a table showing inducing scheme of transdetermining human mesenchymal stem cells to hematopoietic stem cells according to the invention;

FIG. 10 is a table showing sequences of siR-EID1 molecules targeting different loci of EID1mRNA according to the invention comprising SEQ ID NO:7 (GGAGGACGAC-TACGACTATTT), SEQ ID NO:8 (GCATCTGTCTT-GCTGGAAGCT), SEQ ID NO:9 (GGTTGAGCGGTTTG-CACAATG), SEQ ID NO:10 (GGTTTGCACAATGTCGGAAAT), SEQ ID NO:11 (GGCGAGGAATTTGATGACTGG), SEQ ID NO:12 (GC-GAGGAATTTGATGACTGGG), SEQ ID NO:13 (GCTCT-TGAAGAAGCCGACAAG), SEQ ID NO:14 (GA-CAAGATGTTTCTGAGAACA), SEQ ID NO:15 (GGCGGGTTTCAGATGCATTAT), SEQ ID NO:16 (GCGGGTTTCAGATGCATTATG), SEQ ID NO:17 (GGTTTCAGATGCATTATGATT), SEQ ID NO:18 (GGACCCAACTTTCCGCTATCT), SEQ ID NO:19 (GC-CACAGTTATCAAAGGCTAC), SEQ ID NO:20 (GA-CACTAAATGTGTGTGAATG), SEQ ID NO:21 (GCCCA-GAAATTACCTTGGTAT), SEQ ID NO:22 (GCTTGTTATTTGTCATGCACC), SEQ ID NO:23 (GCT-TCAGCTATCTAATTCACA), SEQ ID NO:24 (GCCCTAT-CAATGAGTATGTTG), SEQ ID NO:25 (GCCGTGGT-TACCTTACTAAGA), SEQ ID NO:26 (GCTGAAGTTCTAGGAGAGTAA), SEQ ID NO:27 (GCTCCATTATAGCAGTAAAGA), SEQ ID NO:28 (GAACGAATATCCAATGCAACA), and SEQ ID NO:29 (CAAATACTCACCATTGTGTTA); and FIG. 11 is a table showing amplification medium formula of hematopoietic stem cell according to the invention.

DETAILED DESCRIPTION OF THE INVENTION

Figure 3:
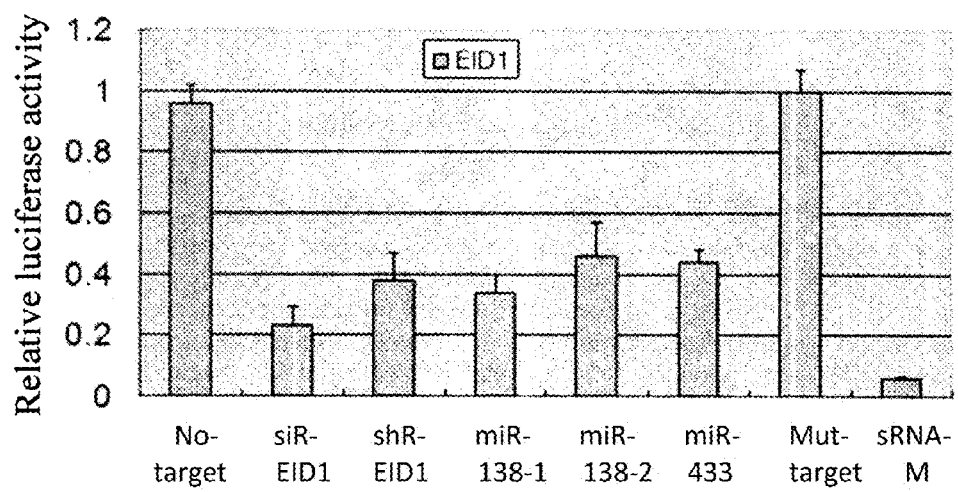
FIG. 3 is the target gene EIDI which can be effectively recognized by different small RNAs molecules according to the invention.
Figure 4:
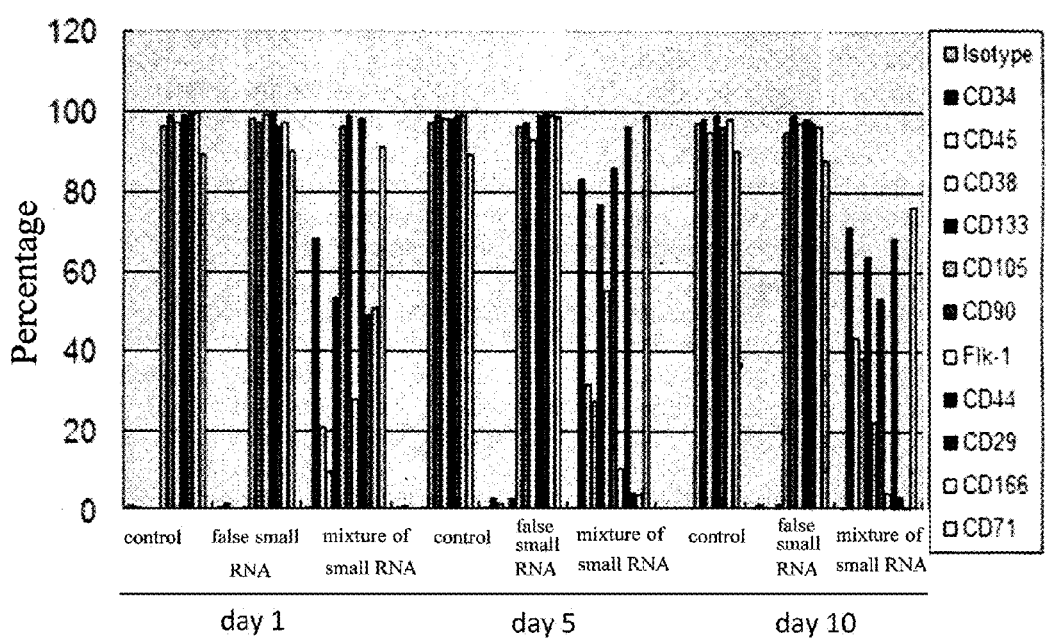
FIG. 4 is the changing of cell surface specific antigens when the human mesenchymal stem cells transdetermined into hematopoietic stem cells according to the invention.

Referring to FIGS. 1 to 11, a method of rapidly inducing large-scale and high-purity mesenchymal stem cells to transdetermine into hematopoietic stem cells, includes the steps as follows: preparation of homogeneous medium of mesenchymal stem cells; combination of a plurality of small RNA molecules; assembling and transfection of nanoparticles of nucleic acids and polypeptides; inducing and amplifying medium of post-transdetermined hematopoietic stem cells; and activating multiple hemopoiesis-related genes.

The medium refers to the medium of adding five factors of EGF, FGF-2, PDGF-BB, IGF and TGF-6 into non-serum high-glucose DMEM/F12 medium. The medium is the medium of adding ten factors of shh, SCF, TPO, Flt3L, Delta1, IGFBP, Angiopoietin, MBP4, LIF, TGF-6 into non-serum high-glucose DMEM/F12 medium. The various small RNA molecules refer to miR-138-1, miR-138-2, miR-433 and siR-EID1 molecule sequence targeting different loci of EID1 mRNA. The siR-EID1 molecule sequence targeting different loci of EID1 mRNA shown in FIG. 10 comprises SEQ ID NO:7 (GGAGGACGACTACGACTATTT), SEQ ID NO:8 (GCATCTGTCTTGCTGGAAGCT), SEQ ID NO:9 (GGTTGAGCGGTTTGCACAATG), SEQ ID NO:10 (GGTTTGCACAATGTCGGAAAT), SEQ ID NO:11 (GGCGAGGAATTTGATGACTGG), SEQ ID NO:12 (GC-GAGGAATTTGATGACTGGG), SEQ ID NO:13 (GCTCT-TGAAGAAGCCGACAAG), SEQ ID NO:14 (GA-CAAGATGTTTCTGAGAACA), SEQ ID NO:15 (GGCGGGTTTCAGATGCATTAT), SEQ ID NO:16 (GCGGGTTTCAGATGCATTATG), SEQ ID NO:17 (GGTTTCAGATGCATTATGATT), SEQ ID NO:18 (GGACCCAACTTTCCGCTATCT), SEQ ID NO:19 (GC-CACAGTTATCAAAGGCTAC), SEQ ID NO:20 (GA- CACTAAATGTGTGTGAATG), SEQ ID NO:21 (GCCCA-GAAATTACCTTGGTAT), SEQ ID NO:22 (GCTTGTTATTTGTCATGCACC), SEQ ID NO:23 (GCT-TCAGCTATCTAATTCACA), SEQ ID NO:24 (GCCCTAT-CAATGAGTATGTTG), SEQ ID NO:25 (GCCGTGGT-TACCTTACTAAGA), SEQ ID NO:26 (GCTGAAGTTCTAGGAGAGTAA), SEQ ID NO:27 (GCTCCATTATAGCAGTAAAGA), SEQ ID NO:28 (GAACGAATATCCAATGCAACA), and SEQ ID NO:29 (CAAATACTCACCATTGTGTTA).

The culture of the post-transdetermined hematopoietic stem cells refers to cultivate at least 3 days as cell density of $5 \times 10^5$/ml in the medium of inducing and amplifying hematopoietic stem cells, and then finally make mesenchymal stem cells to transform into hematopoietic stem cells.

Assembling of nucleic acid and polypeptide nanoparticles refers to preparation process of various small RNA molecules with polypeptide transfection reagents according to the proportion, procedure and time (see example 3), and achieves the optimal inductive efficiency through transfection of once a day, totally 2 times.

The activating multiple hemopoiesis-related genes refers to, but not limited to, Runx1, Bmi1, HoxB4, Gata1, Gata2, Gfi1, Sa114, Pu.1, Scl, Mcl, C-myc, C-myb, Kc14, Cxcr4, and Crb.

Example 1

Separation, Cultivation and Amplification of Hematopoietic Stem Cells

The acquiring of fat/bone marrow/umbilicalcord is carried out under the premise of donor consent. The collection, separation and cultivation of the human fat-derived stem cells: fat aspirates are divided into two components: one is low-density lipid component, and the other is high-density aqueous component, liquid component. The liquid component is used for source of fat-derived stem cells. The acquired adipose tissue is flushed repeatedly 3-5 times by using same volume of PBS under aseptic conditions, adding 0.1% I type collagenase, water-bath shaking at 37° C., digested 60 min, and then a DMEM medium containing 10% fetal calf serum to terminate digestion. Centrifugating at 1000 g for 10 min, the supernatant and the remaining suspension tissue are discarded, resuspending cells, adding 2 times the volume of red blood cell lysis buffer (NH4Cl 154 mmol/L+KHCO.sub.3 10 mmol/L+EDTA 0.1 mmol/L), standing for 10 min, centrifuged and the supernatant is discarded. Washing 3 times with suitable volume of PBS, filtered with 200 mesh screen, the cell suspension is counted using cell counting plate, cell inoculation as $1-3 \times 10^5$ cells/$cm^2$ in a 150 $cm^2$ culture flask, adding with 20 mL of non-serum high-glucose DMEM/F12 medium, adding with 20 ng/ml EGF, 20 ng/ml FGF-2, 10 ng/ml PDGF-BB, 5 ng/ml IGF and 0.5 ng/ml TGF-6, mixed evenly, cultivating in an incubator with 5% saturated humility of $CO_2$ at 37° C.

The medium disclosed by the invention is a fast-amplifying and non-differentiated mesenchymal stem cell culture solution, and it can cultivate highly uniform non-differentiated mesenchymal stem cell, and provide reliable assurance for the follow-up production of hematopoietic stem cells. Using phase-contrast microscope to observe the characters of cell morphology and proliferation conditions, solution was changed for first time after 36-48 h, and changed once 72 h afterwards. When cell fusion is more than 80% of the flask bottom, it is digested with conventional trypsin and then passage.

The identification of human adipose-derived stem cell: picking the 3rd or 4th generation of cell, and then digesting with 0.25% trypsin. Through flow cytometry analysis, it is discovered that ADSCs expresses mainly CD44, CD73, CD90, CD105, CD166, CD29, CD49e and HLA-ABC, but not CD34, CD3, CD19, CD45, CD14, CD31, CD62L, CD95L and HLA-DR (shown in FIG. 1). And the result is almost the same as the results of other MSCs. But there is difference between ADSCs and BMSCs: most BMSCs express CD10 and CD106, while ADSCs expressing CD10 is only 5%-20%; and almost all ADSCs express CD49f and CD54, and BMSCs seldom express those.

Example 2

Sequence, Structure and Synthesis of miRNAs

Through technology of bioinformatics and related prediction software (Target Scan), we scanned and identified three kinds of miRNA (shown in FIG. 2). The first miRNA is miRNA-138-1 having the sequence of SEQ ID NO:1, and the short hairpin DNA sequence corresponding to miRNA-138-1 sequence having the sequence of SEQ ID NO:2 is as follows:

CCCUGGCAUGGUGUGGUGGGGCAGCUGGUGUUGUGAAUCAGGCCGUUGCC

AAUCAGAGAACGGCUACUUCACAACACCAGGGCCACACCACACUACAGG.

The second miRNA is miRNA-138-2 having the sequence of SEQ ID NO:3, and the short hairpin DNA sequence corresponding to miRNA-138-2 sequence having the sequence of SEQ ID NO:4 is as follows:

CGUUGCUGCAGCUGGUGUUGUGAAUCAGGCCGACGAGCAGCG

CAUCCUCUUACCCGGCUAUUUCACGACACCAGGGUUGCAUCA.

The third miRNA is miRNA-433 having the sequence of SEQ ID NO:5, and the short hairpin DNA sequence corresponding to miRNA-433 sequence having the sequence of SEQ ID NO:6 is as follows:

CCGGGGAGAAGUACGGUGAGCCUGUCAUUAUUCAGAGAGGCUAGAUC

CUCUGUGUUGAGAAGGAUCAUGAUGGGCUCCUCGGUGUUCUCCAGG.

All those miRNAs can be acquired by the method of chemistry synthesis, and in order to enhance stability, the composed monomers of those small RNAs can conduct wholly or partly different chemical modification, such as methoxy- or ethoxy-modification. The method of preparation active ingredients of miRNAs of the invention is as follows:

Synthesizing 4 different kinds of nucleotide monomers to three different kinds of small RNA single strands through RNA/DNA synthesizer according to special designed sequence, and the sequences of those small RNA single strands are shown above. The synthesized small RNA single strands are then separated and purified so as to remove other ingredients, and annealed to form three characteristic miRNAs. Those three kinds of miRNA molecules are frozen and concentrated to form dry powder as small nucleic acid active ingredients in the formula, and stored at low temperature. The dry powder includes miRNA-138-1, miRNA-138-2 and miRNA-433, and each miRNA contains a seed fragment of EID1 gene. They respectively co-transfected adipose mesenchymal stem cells together with luciferase plasmid (pRL-TK) containing 3'UTR sequence of EID1, and analysis result of luciferase activity 36 hours after transfection shows that those small RNA molecules (including siR-EID1, shR-EID1 and sRNA-M) can all effectively down-regulate the target gene EID1 (shown in FIG. 3), and can make different histone acetylation and multiple transcription factors acetylation, consequently active mesenchymal stem cells and make them transform to other stem cells easily. In order to enhance interference effect of small RNAs, we adopt the combined strategy of those three kinds of small RNAs (sRNA-M), and the final active ingredients of small nucleic acids are mixed and prepared according to the proportion of 1:1:1 by dry powder weight after the synthesis of miRNA-138-1, miRNA-138-2 and Example 3

The Preparation and Cell Transfection of Nanoparticles of Small Nucleic Acids and Polypeptides Mixture of above-mentioned small nucleic acid ingredients and cell penetrating peptide (bought from Beijing Giliao Biotechnology Development Co., Ltd.) are dissolved respectively in medical-grade deionized water, evenly mixed for 10 min, and then slowly dripping the solution of small nucleic acid ingredients into the solution of cell penetrating peptide under stirring state, according to ratio of nucleic acid to peptide, es. 1:10 to 1:100. Keep stirring and enable small nucleic acid ingredients and cell penetrating peptide to mix fully, standing for 20 min, and then make them fully self-assemble into nanoparticles, and then ready to use.

In order to improve the determining efficiency of small RNAs of inducing human mesenchymal stem cells to hematopoietic stem cells, the invention further optimizes detailed inducing schemes, here are disclosed 8 kinds of inducing formula as shown in FIG. 9. From the table, it can be seen that the efficiency of second inducing formulation of scheme 3 is highest, and it can enable 80% of human mesenchymal stem cells transdetermine to hematopoietic stem cells, es. through transfection once a day, totally 2 times. It is greatly improved than our original induction method, so that this technology can make it possible to obtain clinical-grade stem cells. And it can be further used to treat blood diseases such as aplastic anemia and leukemia.

Example 4

Small Nucleic Acid-Peptide Nanoparticles Inducing Mesenchymal Stem Cells Transdetermine to Hematopoietic Stem Cells 1 to 2 days after transfecting of miRNA-433 and miR-138 into human mesenchymal stem cells, adherent spindle mesenchymal stem cells transform into suspended round stem cells. It is cultivated at least 3 days as the cell density of $5\times10^5$/ml in the medium (formula shown in FIG. 11) of inducing and amplifying of hematopoietic stem cells, and these stem cells lose gradually the specific antigens (e.g., CD44, CD73, CD105, CD166, CD29, and Flk-1) of mesenchymal stem cell and acquire meanwhile the surface antigen (e.g., CD34, CD133, CD49f, CD38, CD45, CD41 and CD90) (shown in FIG. 4) of hematopoietic stem cell. And then they acquire quick amplification.

Figure 5:
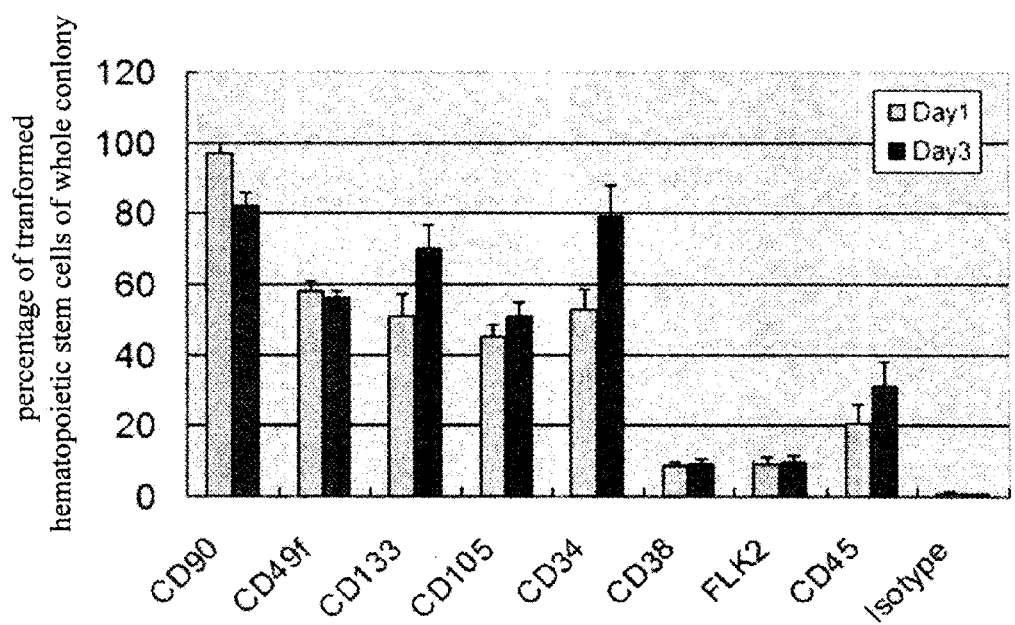
FIG. 5 is the classification and proportion of the transdetermined hematopoietic stem cells and hematopoietic progenitor cells according to the invention.

Analyzing these transformed stem cells through FACS double-antigen labeling, and the result shows that in these stem cells, 90% of these cells express surface antigens (e.g., CD34, CD133, CD150, CD49f, CD45, CD41 and CD90) of long-term hematopoietic stem cells (LT-HSCs) and short-term hematopoietic stem cells (ST-HSCs), and only 10% of these cells express surface symbolic antigens (e.g., CD38 and FLK2) of hemopoietic progenitor cell (shown in FIG. 5).

Figure 6:
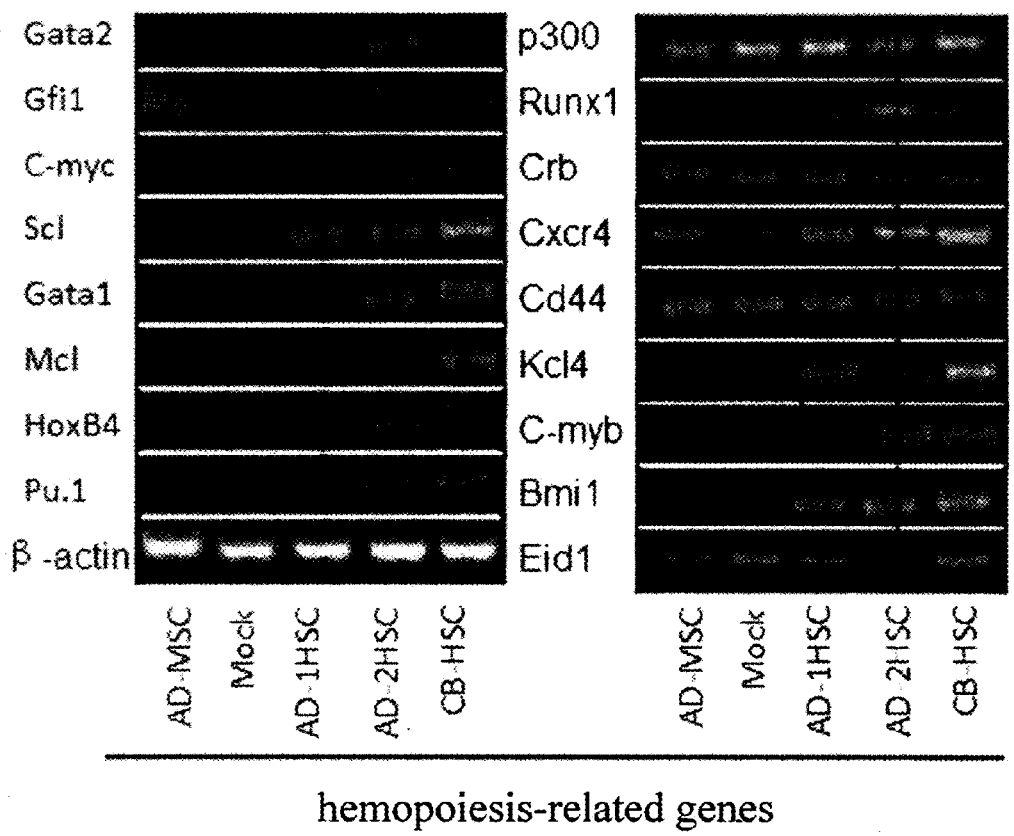
FIG. 6 is the PCR electrophoretic analysis comparing expression difference of hematopoiesis-related genes in human mesenchymal stem cells, hematopoietic stem cells, and stem cells transfected with different small RNA molecules according to the invention.
Figure 7:
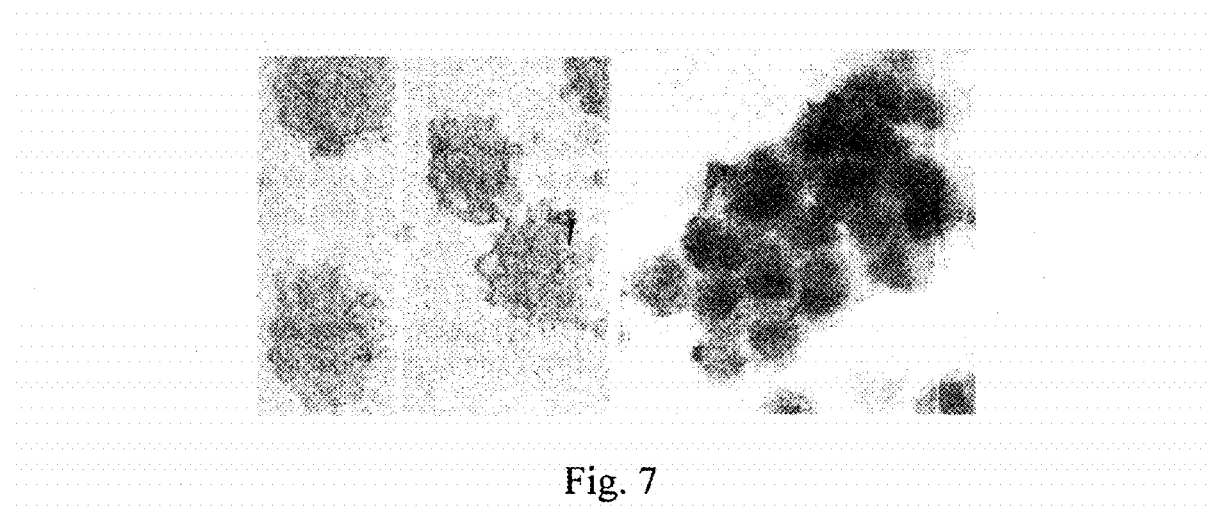
FIG. 7 is colony formation and cellular morphology of transdetermined hematopoietic stem cells according to the invention.
Figure 8:
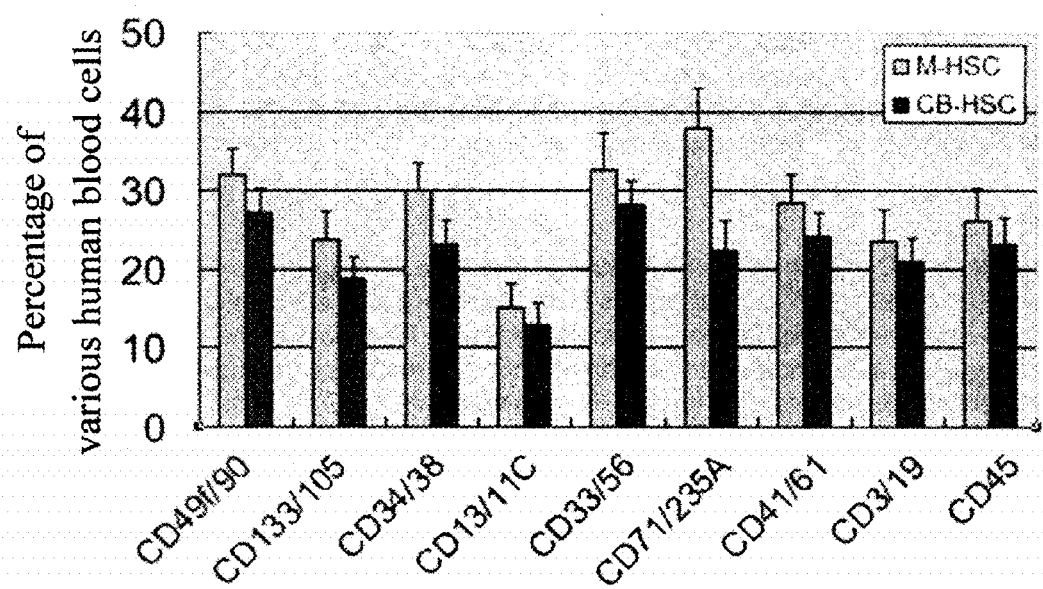
FIG. 8 is the condition of the second-implantation and differentiation to various blood cells of the transdetermined hematopoietic stem cells and hematopoietic progenitor cells in mice according to the invention.

To detect these transformed stem cells with the method of RT-PCR, and then discovered that they can highly express many important hematopoiesis-related gene, such as Runx1, Bmi1, HoxB4, Gata1, Gata2, Gfi1, Sal14, Pu.1, Scl, Mcl, C-myc, C-myb, Kc14, Cxcr4, and Crb, and hence make them more similar with nature-occurred hematopoietic stem cells at the aspect of gene expression, and different with mesenchymal stem cells which they come from (shown in FIG. 6). The activation of these critical hematopoiesis-regulated genes enables mesenchymal stem cells to transdetermine into hematopoietic stem cells.

In order to verify that these transformed single cells can self-renew through cultivation, the transfected single cells are separated and then inoculated on the 24-hole culture plate (bought from Corning company) covered with methyl cellulose, and adding cytokines of inducing hematopoietic stem cells to amplify and other necessary ingredients (formulation shown in FIG. 11), and the cultivation condition: 37° C., 5% CO2. The formulation of the medium of the invention which induces hematopoietic stem cells to amplify is shown in FIG. 11. Observed on the 15th day, it can be seen the formation of cell colony (shown in FIG. 7). And the method is more efficient and quicker compared with cultivated method of colonies of hematopoietic stem cells used widely nowadays. The cultivated method usually used easily leads to differentiation of hematopoietic stem cells and hemopoietic progenitor cells and lower multiple of amplification.

Example 5

Two-Time Transplantation Experiment Shows these Transformed Hematopoietic Stem Cells can Rebuild Hematopoietic Function Mesenchymal stem cells tranfected with small RNA molecules are respectively transplanted into mice which are treated by radiation of lethal dose. Hematopoietic cells differentiated from human adipose-derived mesenchymal stem cells can be detected after 10 weeks. And then hematopoietic stem cells differentiated from human adipose-derived mesenchymal stems are separated from murine bone marrow, and are transplanted into other mice treated by radiation of lethal dose again. Murine bone marrow is analyzed by FACS through anti-human monoclonal antibody after 10 weeks, and then it is found that the expression of gene symbolic molecules of hematopoietic stem cells and hemopoietic progenitor cells can be detected in the bone marrow of the mice treated by radiation of lethal dose. These hemopoietic progenitor cells can further differentiate to blood cells which specifically express the molecule markers such as CD33, CD13, CD19, CD3, CD235, CD61, and CD56, etc. (shown in FIG. 8). And it is visible that the induced hematopoietic stem cells can be used in treating blood diseased such as aplastic anemia and leukemia.

Due to adoption of the above-mentioned technical solution, a method rapidly inducing large-scale and high-purity mesenchymal stem cells to transdetermine into hematopoietic stem cells, which includes the steps as follows: 1) preparation of homogeneous medium of mesenchymal stem cells; 2) combination of a plurality of small RNA molecules; 3) assembling and transfection of nanoparticles of nucleic acids and polypeptides; 4) inducing and amplifying medium of post-transdetermined hematopoietic stem cells; and 5) activating multiple hemopoiesis-related genes. It solves the bottleneck question of difficulty of cell matching, immune rejection and quantity limitation of hematopoietic stem cells in treatment of hematopoietic stem cells in existing technique. The induced hematopoietic stem cells can be used in treating blood diseased such as aplastic anemia and leukemia.

The invention provides some endogenous miRNAs and the derivatives thereof, they are different from the shRNAs whose fragments of stems and loops are totally complementary introduced in our former patent. It is a totally new resource of hematopoietic stem cells, and has much higher transformation efficiency, and the efficiency is 8-10 times than that of our former patent, and enables the clinical application. It resolves effectively the bottleneck question of efficient transfection small RNAs into primary mesenchymal stem cells, and prevents effectively the occurrence of easy differentiation of hematopoietic stem cells into downstream blood cells during the process of amplification of hematopoietic stem cells, and activate effectively multiple genes related to occurrence of hematopoietic stem cells.

While the invention has been described in terms of preferred embodiments, those skilled in the art will recognize that the invention can be practiced with modifications within the spirit and scope of the appended claims.

What is claimed is:

1. A method of inducing mesenchymal stem cells to transdetermine into hematopoietic stem cells, comprising the steps of:
   (a) preparing a homogeneous culture of mesenchymal stem cells in a non-serum high-glucose Dulbecco's modified Eagle's medium (DMEM) medium comprising epidermal growth factor (EGF), fibroblast growth factor-2 (FGF-2), platelet-derived growth factor subunit B (PDGFB), insulin-like growth factor (IGF), and transforming growth factor (TGF)-beta;
   (b) providing a mixture of RNA molecules comprising miR-138-1 and a siR-EID1 (small interfering RNA-EP300-interacting inhibitor of differentiation 1);
   (c) assembling nanoparticles comprising the mixture of RNA molecules in step (b) and cell penetrating polypeptides;
   (d) transfecting the nanoparticles of step (c) into the culture of mesenchymal stem cells; and (e) inducing and amplifying hematopoietic stem cells from the transfected mesenchymal stem cells in a non-serum high-glucose DMEM medium comprising sonic hedgehog (shh), stem cell factor (SCF), thyroid peroxidase (TPO), fibromyalgia syndrome-like tyrosine kinase 3 ligand (Flt3l), delta-like protein 1 (Delta1), insulin-like growth factor-binding protein (IGFBP), angiopoietin, myelin basic protein 4 (MBP4), leukemia inhibitory factor (LIF), and TGF-beta factors to activate a plurality of hemopoiesis-related genes.

* * * * *